United States Patent [19]
Gottlieb

[11] Patent Number: 4,751,216
[45] Date of Patent: Jun. 14, 1988

[54] METHODS FOR TREATING AIDS AND ARC

[75] Inventor: A. Arthur Gottlieb, New Orleans, La.

[73] Assignee: Imreg, Inc., New Orleans, La.

[21] Appl. No.: 83,437

[22] Filed: Jul. 16, 1987

Related U.S. Application Data

[63] Continuation of Ser. No. 813,632, Dec. 26, 1985, Pat. No. 4,699,898.

[51] Int. Cl.$^4$ .............................................. A61K 37/02
[52] U.S. Cl. ........................................ 514/18; 514/19
[58] Field of Search .................. 424/85; 514/2, 18, 19

[56] References Cited

U.S. PATENT DOCUMENTS

| | | | |
|---|---|---|---|
| 4,537,878 | 8/1985 | Plotnikoff | 514/2 |
| 4,699,898 | 10/1987 | Gottlieb | 424/85 |

*Primary Examiner*—Delbert R. Phillips
*Attorney, Agent, or Firm*—Richard H. Stern

[57] ABSTRACT

Methods are disclosed for the treatment of Acquired Immune Deficiency Syndrome (AIDS) and AIDS-Related Complex (ARC) by administering injections of Tyr-Gly-Gly and derivatives thereof.

20 Claims, No Drawings

METHODS FOR TREATING AIDS AND ARC

This is a continuing patent application based on the disclosure contained in copending U.S. Ser. No. 813,632, now U.S. Pat. No. 4,699,898, "Tripeptides affecting immune response," filed Dec. 26, 1985 (which priority date is claimed herein) and declared allowable June 10, 1986. Claims in that application relating to the treatment of AIDS were subject to a restriction requirement and are now pursued herein.

BACKGROUND

Amplifiers derived from white blood cells have been shown to amplify immune system response in human and animal subjects. As suggested, for example, in issued U.S. Pat. Nos. 4,616,079 and 4,468,379, and in copending U.S. patent applications Ser. Nos. 902,683 and 813,632, amplifiers appear to act on T-helper cells (T4+ or T4 cells) in a way that causes them to produce chemical mediators whose effect is to increase the speed and/or magnitude of the cell-mediated immune system response to antigens, mitogens, and other means for activating a cell-mediated immune system response. Indicia of this response include enhancement of delayed hypersensitivity (DH) reactions to recall antigens, production of IL-2 and gamma-interferon, and potentiation of cytotoxic cells.

It is known that the human diseases or pathological conditions known as Acquired Immune Deficiency Syndrome (AIDS) and AIDS-Related Complex (ARC) depress the immune system response. As a result the affected patient becomes more susceptible to opportunistic infections, malignancies, or other pathological conditions against which a normal immune system would have protected the patient. Other background information on amplifiers, AIDS, and ARC is found in the specification of the parent application on which this application is based and in the other references cited in the preceding paragraph.

SUMMARY

The inventor has discovered that the administration to AIDS and ARC patients of materials containing the amino acid residue sequence Tyr-Gly-Gly alleviate certain symptoms associated with AIDS and ARC, reverse certain pathological effects associated with AIDS and ARC, and appear to improve the clinical condition of the patients so treated. Such treatment does not cure AIDS or ARC, but does appear therapeutically useful in slowing progression of the diseases and alleviating symptoms.

DETAILED DESCRIPTION OF PREFERRED EMBODIMENTS

As stated in greater detail in the parent application, the inventor has isolated from human leukocyte dialysates certain materials naturally occurring in very dilute concentrations. The effective dosage amount of the materials of this invention, very approximately 80 pg for an adult male, is derived from approximately $4 \times 10^5$ leukocytes. The term "material" is used herein, rather than "product," to avoid any implication that the subject matter of the invention is a single known molecular species. Two materials are described in the parent application, TGG-compound and Molecule Z. In the copending Ser. No. 902,683 application, a third material, TG-material, is described.

TGG-compound is described in the parent application as a molecule or complex containing the amino acid residue sequence Tyr-Gly-Gly and no further amino acid residues. As defined, TGG-compound includes Tyr-Gly-Gly per se and pharmaceutically acceptable salts, amides, esters, complexes, compounds, and protected derivatives of Tyr-Gly-Gly. It also includes Tyr-Gly-Gly bound to a sugar, such as ribose, or another moiety having fewer than 12 carbon atoms. It also includes Molecule-Z, defined below.

Molecule Z is described in the parent application as a material extracted from human leukocyte dialysates and found to contain Tyr-Gly-Gly plus other things. It is still uncertain what Molecule Z is, because analytic tests have not been successful in characterizing it precisely in terms of chemical composition. The data available at this time suggests that Molecule Z may be a mixture, complex, or dimeric form of materials containing the amino acid residue sequences Tyr-Gly and Tyr-Gly-Gly. It may also be Tyr-Gly-Gly bound to a sugar or other moiety. Thus, so-called Molecule Z may or may not be a single molecule. Since Molecule Z elutes from HPLC after Tyr-Gly-Gly using a water-ethanol gradient (see Example 3 of parent application), it may be presumed that Tyr-Gly-Gly is the smaller molecule of the two. Amino acid analysis of Molecule Z revealed the presence only of Tyr and Gly groups (see Example 4 of parent application).

TG-material is described in the '683 application as a molecule or complex containing the amino acid residue sequence Tyr-Gly and no further amino acid residues. As defined, TG-material includes Tyr-Gly per se and pharmaceutically acceptable salts, amides, esters, etc. of Tyr-Gly.

The inventor has carried out tests in over 100 AIDS and ARC patients, primarily with a product known as Imreg-1 ™ or Beta-1.0. That product has been further purified and found to contain immunologically active materials having Tyr-Gly and Tyr-Gly-Gly amino acid residue sequences. Beta-1.0 also contains TGG-compound, Molecule Z, and TG-material, as those terms are defined above. The therapeutic results accomplished in these tests are described below. The AIDS and ARC tests were preceded by tests establishing that Beta-1.0 was immunologically active as an amplifier in delayed type hypersensitivity skin tests (DH tests) and in other indicia of immunoamplifier activity; other similar tests showed the immunological activity of the TGG-compound, Molecule Z, and TG-material components of Beta-1.0 as immunoamplifiers.

The tests described below indicate that an effective dosage amount for systemic human immunoamplifier purposes is approximately $10^6$ times the dosage for maximal dermal response in a DH test, administered every two weeks. Thus an effective human dosage amount is approximately 80 pg for a 70 kg adult, or 1.2 pg per kg of body weight, every two weeks. That amount is approximately 300 femtomoles (fM) for Tyr-Gly-Gly or Tyr-Gly. The appropriate dosage amount for a particular patient, however, is necessarily a matter of judgment for the attending physician, and it may well be appropriate to begin a therapeutic regimen with a much higher dosage, such as 300 pg on a weekly basis. It may also be appropriate to maintain a patient on a lower dosage.

Phase I and II Studies

The FDA authorized the inventor to carry out Phase I and II studies with AIDS and ARC patients to assist in determining safety and efficacy of Beta-1.0 in the treatment of AIDS and ARC. Studies were carried out in several institutions, involving over 100 patients. These studies have now been extended to Phase III, with the permission of FDA, to additional patients, and it is anticipated that these studies will be completed in 1987. Thus far, no observable toxicity has been found, and beneficial therapeutic results were found as described below.

The following examples are based on data from the Phase I-II studies.

EXAMPLE 1

Multiple Doses of Beta-1.0: Group 1

The members of a group of 15 patients with AIDS received one standard dose of Beta-1.0 once every month until three doses were given (three months). Of these 15 patients, six had candida infections (oral candidiasis), and 12 had Kaposi's Sarcoma.

Clinical symptoms were monitored. No decrease in weight was observed. No toxicity to Beta-1.0 was observed.

A significant decrease in candida infection was observed as a result of treatment, in three-quarters of the patients completing the protocol.

Skin test sensitivity (DH test) to tetanus toxoid was noticeably enhanced, and returned to an approximately normal level in 47% of the subjects. Since, according to the Walter Reed Classification of Severity of AIDS-/ARC (see 314 New Eng. J. Med. 131 (1986)), candida infection and loss of skin test sensitivity are signs of far advanced immunodeficiency, the effectiveness of Beta-1.0 in reversing these symptoms is medically significant.

Mitogen-stimulated lymphoctye proliferation increased with each successive dose. Mitogen-stimulated IL-2 production increased in at least 60% of patients. Response to pokeweed mitogen (PWM) increased for those patients having more than 50-100 T4 cells per $mm^3$ remaining.

EXAMPLE 2

Multiple Doses of Beta-1.0: Group 2

The members of a group of 14 patients with AIDS received one standard dose of Beta-1.0 every two weeks for six doses (approximately three months). Of these subjects, six had candida infections. Of the 14 patients, 11 had Kaposi's Sarcoma.

Clinical symptoms were monitored. Eleven of the 14 patients gained weight. An average weight gain of 4.4 lb occurred in these 11. No toxicity to Beta-1.0 was observed. Serum uric acid levels fell. Creatine phosphokinase levels fell. Since high levels of uric acid and creatine phosphokinase reflect tissue breakdown characteristic of AIDS, lowering of the levels of these substances and reversal of weight loss suggests significant clinical improvement.

Skin test sensitivity to tetanus toxoid returned in 57% of subjects. Candida infection was totally cleared in three subjects and decreased in another.

Mitogen-stimulated lymphocyte proliferation increased. Mitogen-stimulated IL-2 production increased in 60% of patients after two doses of Beta-1.0; and in all those patients having more than 50-100 T-helper cells/$mm^3$ remaining, after two doses of Beta-1.0.

Response to pokeweed mitogen (PWM) increased for those patients having more than 50-100 T-helper cells/$mm^3$ remaining. A small increase to PWM appeared after the second dose with those patients having fewer than 50-100 T-helper cells/$mm^3$ remaining, and slowly increased following the next two doses.

There was also a slowing of the rate of destruction of T-helper cells during the treatment with Beta-1.0. For example, untreated patients with ARC typically lose T-helper cells at the rate of approximately 13.4 cells/month. For those of the above ARC patients who received Beta-1.0 on a monthly basis (Example 1), the rate of T-helper cell loss was 7.2 cells/month, while for those who received it every two weeks (Example 2) the rate of T-helper cell loss was 4.2 cells/month. This data indicates that Beta-1.0 slows the rate of T-helper cell destruction typical of ARC. The retarding of destruction is proportional here to the dosage.

EXAMPLE 3

Multiple Doses of Beta-1.0: Group 3

Five patients, three with AIDS (RB, JB, and RG) and two with ARC (WW and CM) were treated with Beta-1.0 over a period of approximately a year or more. (One standard dose intradermally every two weeks.)

Skin test sensitivity returned completely in three subjects and partially in one (RB, JB, WW, and CM). Candida infection improved in the two patients (RB and CM) initially having it and it did not appear in the others. The percentage of T-helper cells increased transiently in four patients (RB, RG, WW, and CM).

Three patients gained substantial weight (RB, WW, and CM). PHA-stimulated lymphocyte proliferation increased in all five, PWM response in four (RB, RG, WW and CM), IL-2 production in three (RB, WW, and CM).

These tests indicate that Beta-1.0 has a positive effect on the T-helper cell population of the human body and is useful in improving human immune response characterized by a T-helper cell defect. Doses of Beta-1.0 appear to partially restore the functioning of a defective subset of the T-helper lymphocytes. Tests such as those on patient DT suggest that Beta can partially correct a defect in T-helper cell function even in the presence of the excessive proportions of T8+ cells observed in AIDS patients.

It appears, further, that some minimal level of residual T-helper cell function must be present for Beta to improve immunological functions; if T-helper cell loss is too severe, there may not be enough T-helper cells left to respond to doses of Beta as a lymphokine and thus be immunologically reconstituted. The data above suggest that when the T-helper cell population falls below approximately 100 cells/$mm^3$, it may be difficult or impossible to reconstitute immunological function.

The following example is based on composite data.

EXAMPLE 4

Treatment of AIDS or ARC

An adult male patient, 70 kg, has an immunodeficient condition resulting from AIDS or ARC. The attending physician is concerned that the patient may become subject to opportunistic infections and desires to increase the patient's immune system activity.

Based on the condition of the patient, the physician determines a dosage amount that in his or her medical judgment is appropriate, such as 300 pg of TGG-compound, Molecule Z, or TG-material every week. The physician administers this dosage amount by subcutaneous or intradermal injection.

The physician monitors the patient's immune function by weekly blood tests measuring the patient's immune capability. Monthly testing by injection of a recall antigen (such as tetanus toxoid) is also carried out.

The physician monitors the patient's progress, and increases or decreases the dosage amount as indicated by his or her medical judgment.

CONCLUDING REMARKS

It is known that endogenous mammalian polypeptides, such as Tyr-Gly-Gly-Phe-Met and Tyr-Gly-Gly-Phe-Leu, are enzymatically cleaved in the body to produce such metabolites as Tyr-Gly and Tyr-Gly-Gly. It is also known that insertion of a D-aminoacid such as D-Ala into a dipeptide such as Tyr-Gly, thereby producing the tripeptide Tyr-D-Ala-Gly, may inhibit such enzymatic action. It is also known that other expedients exist to inhibit enzymatic degradation of peptides, such as N-methylation of the Tyr residue, insertion of a D-aminoacid at or near the C-terminal end of the amino acid residue sequence, esterification of the terminal carboxyl, mixture with bacitracin, puromycin, bestatin, amastatin, or thiorphan.

It is also known to bind or complex an inhibiting agent to a pharmaceutically active molecule, so that the inhibiting agent will preferentially bind to the active site on the enzyme to be inhibited, thereby preempting the site and keeping the enzyme from hydrolyzing the pharmaceutically active molecule. Sulbactam, a beta lactamase inhibitor, is an example of the latter. It is used to protect ampicillin from beta lactamase by mixing ampicillin and sulbactam (sold as Unasyn TM, Pfizer) or by complexing or otherwise linking the ampicillin and sulbactam via an ester (sold as sultamicillin). It is also known, in the case of the synthetic penicillins, to introduce a large moiety (such as $CH_3$ or $NH_2$) at a location on the penicillin where there would otherwise be a space providing a site for enzyme attachment to the penicillin and resulting hydrolysis.

The foregoing information suggests two possibilities germane to this invention. First, a product of this invention such as Tyr-Gly-Gly may be delivered to an AIDS patient in a form such as Tyr-Gly-Gly-X or Tyr-Gly-Gly-X-Y, where endogenous enzymes will cleave the product delivered to the AIDS patient into Tyr-Gly or Tyr-Gly-Gly moieties, among others. It is considered that to do so would be to evade the protection of the patent sought herein, while appropriating its teachings, and that doing so should therefore be considered within the scope of this invention. Accordingly, that expedient is claimed hereinafter. It should be noted that products of the form Tyr-Gly-Gly-X-Y can be endogenous or non-endogenous.

The second point is that it would be appropriate to protect products of this invention from metabolic degradation by using the known pharmaceutical expedients described above. It is therefore considered within the scope of this invention to bind, complex, or mix an inhibitor along with the products of this invention, in a pharmaceutical composition. As used in the claims, the term "with an inhibitor" refers to any of the following: binding or complexing an inhibitor to a product of the invention, to inhibit enzymatic degradation of said product; mixing an inhibitor with a product of this invention for said purpose; inserting a D-aminoacid into the amino acid residue sequence of a product of this invention for said purpose; otherwise engaging in known types of molecular manipulation of the products of this invention in order to inhibit enzymatic degradation, such as N-methylation of the Tyr residue, insertion of a D-aminoacid at or near the C-terminal end of the amino acid residue sequence, and esterification of the terminal carboxyl.

As used in the claims, a composition containing TGG-compound would include a composition containing Beta-1.0, since it is known from the parent patent application that Beta-1.0 contains TGG-compound. It should be noted that Beta-1.0 also contains TG-material and Molecule Z. A composition should be considered to contain Tyr-Gly-Gly or Tyr-Gly even where said peptides are present in a complexed or dimeric form, such as (Tyr-Gly)Zn++(Tyr-Gly-Gly) or (Tyr-Gly)(Gly-Tyr).

As used in the claims, a D-aminoacid "inserted adjacent to a Gly residue" means a D-aminoacid inserted into the amino acid residue sequence to the right (C-terminal side) or left (N-terminal side) of a Gly residue. For example, in the case of Tyr-Gly-Gly and D-Ala, that would produce any of the following: Tyr-D-Ala-Gly-Gly, Tyr-Gly-D-Ala-Gly, Tyr-Gly-Gly-D-Ala.

The subject matter claimed is as follows:

1. A method of treating an AIDS or ARC patient to improve said patient's immune response, comprising administering to said patient a pharmaceutically acceptable composition containing an effective dosage amount of at least one of the following: TGG-compound, Molecule Z, or TG-material.

2. A method of treating an AIDS or ARC patient to improve said patient's immune response, comprising administering to said patient an effective dosage amount of at least one of the following—TGG-compound, Molecule Z, or TG-material—with an inhibitor.

3. A method of treating an AIDS or ARC patient to improve said patient's immune response, comprising administering to said patient an effective dosage amount of a product that metabolizes within the body of said patient to at least one of the following: TGG-compound, Molecule Z, or TG-material.

4. The method of claim 1 wherein said TGG-compound is Tyr-Gly-Gly.

5. The method of claim 2 wherein said TGG-compound is Tyr-Gly-Gly.

6. The method of claim 3 wherein said TGG-compound is Tyr-Gly-Gly.

7. The method of claim 1 wherein said TG-material is Tyr-Gly.

8. The method of claim 2 wherein said TG-material is Tyr-Gly.

9. The method of claim 3 wherein said TG-material is Tyr-Gly.

10. The method of claim 1 wherein said composition essentially contains TGG-compound and TG-material.

11. The method of claim 10 wherein said TGG-compound is Tyr-Gly-Gly and said TG-material is Tyr-Gly.

12. The method of claim 1 wherein said composition essentially contains TGG-compound.

13. The method of claim 12 wherein said TGG-compound is Tyr-Gly-Gly.

14. The method of claim 1 wherein said composition essentially contains TG-material.

15. The method of claim 14 wherein said TG-material is Tyr-Gly.

16. The method of claim 1 wherein said dosage amount is from 0.01 to 100 pg per kg of body weight, administered weekly or biweekly by subcutaneous or intradermal injection.

17. The method of claim 2 wherein said inhibitor is a D-aminoacid residue inserted adjacent to a Gly residue.

18. The method of claim 17 wherein said D-aminoacid residue is D-Ala.

19. The method of claim 3 wherein said product is non-endogenous.

20. The method of claim 3 wherein said product is a polypeptide free of Met and Leu residues in the amino acid residue sequence thereof.

* * * * *